United States Patent [19]
Newton, III

[11] 3,975,778
[45] Aug. 24, 1976

[54] TOTAL ANKLE ARTHROPLASTY
[76] Inventor: St. Elmo Newton, III, 801 Broadway, Seattle, Wash. 98122
[22] Filed: July 14, 1975
[21] Appl. No.: 595,518

[52] U.S. Cl. .................................. 3/1.91; 128/92 C
[51] Int. Cl.² ............................................ A61F 1/24
[58] Field of Search ............................ 3/1.9–1.911, 3/1; 128/92 C

[56] References Cited
UNITED STATES PATENTS

| | | | |
|---|---|---|---|
| 3,839,742 | 10/1974 | Link | 3/1.91 |
| 3,872,519 | 3/1975 | Giannestras et al. | 3/1 |
| 3,889,300 | 6/1975 | Smith | 3/1.91 |
| 3,896,503 | 7/1975 | Freeman et al. | 3/1.91 |

*Primary Examiner*—Ronald L. Frinks
*Attorney, Agent, or Firm*—Seed, Berry, Vernon & Baynham

[57] ABSTRACT

A total ankle arthroplasty comprising a high-density polyethylene tibial unit having a concave surface forming a portion of a cylinder, a lower Vitallium talar unit having a convex bearing surface forming a portion of a sphere of a radius less than the radius of the concave surface of the tibial unit. The tibial unit has an upper portion provided with roughening, grooves and holes for improving the cementatious adherence between the tibial unit and the tibia. The talar unit has grooves and holes for also improving the cementatious adherence between the talar unit and the talus.

4 Claims, 3 Drawing Figures

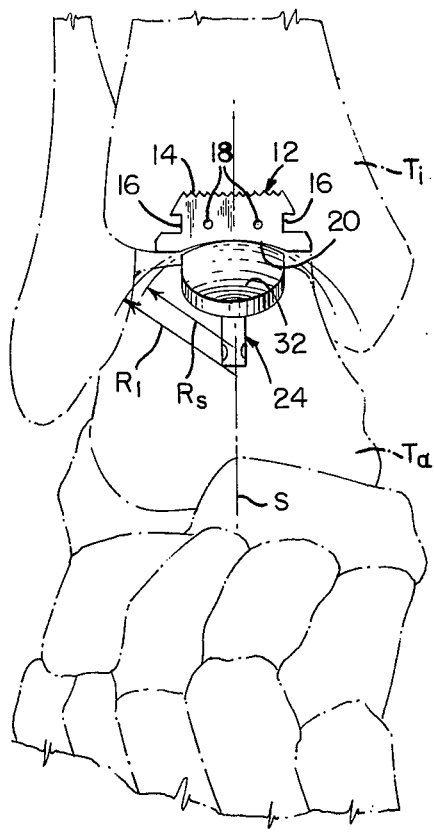
FIG. 1
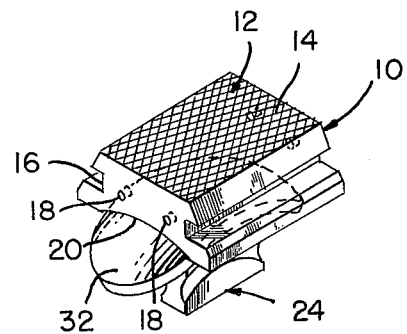
FIG. 2
FIG. 3
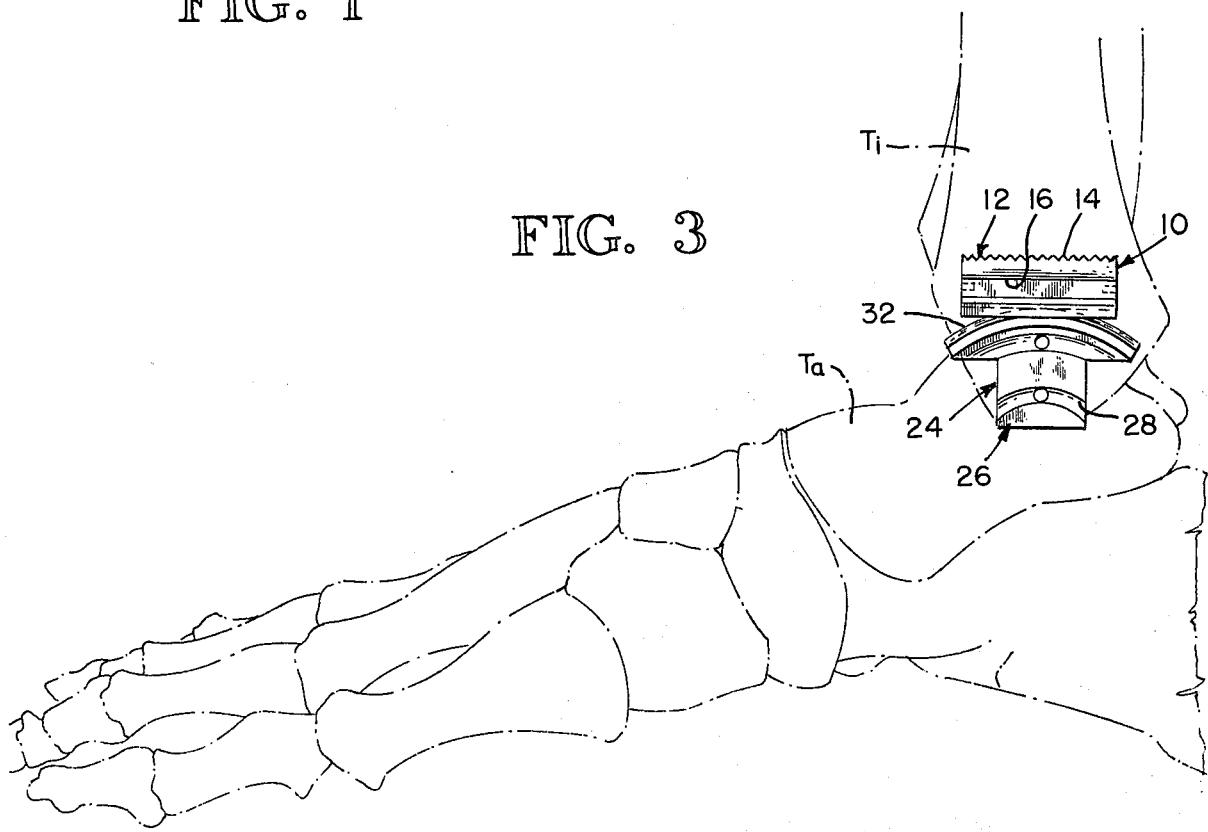

TOTAL ANKLE ARTHROPLASTY

BACKGROUND OF THE INVENTION

1. Field of the Invention

This invention relates to ankle prosthesis.

2. Description of the Prior Art

The ankle joint is a frequent source of disability in patients with rheumatoid arthritis, post-traumatic degenerative arthritis and, occasionally, avascular necrosis of the talus. Adequate malleoli and ligamentous stability are mandatory for proper functioning of an ankle prosthesis.

Fusion has been the common treatment for the severely painful arthritic ankle joint, sacrificing motion in order to gain pain relief. In addition, literature reveals that ankle fusion has additional problems of non-union, infection, loss of position and need for repeat surgery. A solid ankle fusion places an additional strain on the knee and tarsal joints on that same side. If problems exist in these joints, as in rheumatoid arthritis, this added strain can cause their symptoms to become steadily worse. If no problems exist, painful degenerative changes frequently occur in the talonavicular joint.

SUMMARY OF THE INVENTION

It is an object of this invention to provide a total ankle prosthesis which provides increased mobility of the ankle joint and relief of ankle pain.

It is another object of this invention to provide a total ankle prosthesis which allows inversion, eversion, extension and flexion.

Basically, these objects are obtained by providing, in the broadest aspect, a two-part device comprising an upper tibial unit having an arcuate bearing surface and a lower talar unit having an upper arcuate bearing surface. Preferably, the bearing surface of the tibial unit is concave and forms a portion of a cylinder, with the longitudinal axis of the cylinder lying generally in the sagittal plane. Preferably, the bearing surface of the talar unit is a portion of a sphere having a radius less than the radius of the cylindrical portion of the tibial unit. In this manner, the bearing surfaces are free to rock against one another, as well as provide arcuate and linear sliding and rotational movement. These various forms of movement provide increased flexibility in the ankle joint, giving the foot more freedom of movement and minimized discomfort to the patient. In addition, the insertion technique for placing the tibial and talar units in place and against each other is greatly simplified.

The smaller radius of the sphere is advantageous in that imperfect placement of the units does not change the articulation or compromise the result.

The normal ankle is not a hinge joint, but rather has a polycentric motion much like the knee which includes both gliding (arcuate sliding) and slight rotation. This prosthesis allows all these motions.

BRIEF DESCRIPTION OF THE FIGURES OF THE DRAWING

FIG. 1 is an anterior elevation showing the bones of the ankle and foot in phantom lines and the ankle arthroplasty of this invention in solid lines.

FIG. 2 is an isometric of the foot and ankle arthroplasty.

FIG. 3 is a side elevation of the arthroplasty in slightly more detail.

DETAILED DESCRIPTION OF THE PREFERRED EMBODIMENT

The total ankle arthroplasty is a two-part device. The arthroplasty includes a tibial unit 10 having an upper portion 12 that is provided with a roughened upper surface 14, a pair of grooves 16 and holes 18. The roughened surface, grooves and holes are provided to improve the securement between the tibial unit and the tibia Ti. Preferably, the securement is by the use of Simplex P Methylmethacrylate cement or any other suitable surgical cement. The tibial unit is provided with a lower concave bearing surface 20 formed in the shape of a partial cylinder having a radius $R_1$. The tibial unit is secured to the tibia with the longitudinal axis of the partially cylindrical surface lying generally in the sagittal plane S and centered over the articular surface of the talus Ta.

The talar unit 24 is preferably made of Vitallium or other suitable material and is provided with a lower portion 26 having a plurality of grooves 28 and holes for providing increased securement to the talus through the use also of the Methylmethacrylate cement. The upper portion of the talar unit 24 is provided with a bearing surface 32 that forms a portion of a sphere of a radius $R_s$ which is less than the radius $R_1$. Thus, as best shown in FIGS. 1 and 3, the bearing surface of the talar unit can rock in any vertical plane. In addition, the bearing surfaces can slide or glide relative to one another. That is, the bearing surfaces can slide linearly relative to one another in the sagittal plane and can slide arcuately relative to one another in all planes. Still further, the bearing surfaces can rotate about a vertical axis relative to one another. It is an important feature of this invention that these varied and multiple forms of relative motion provide a maximum amount of articulation between the tibia and talus so that the patient has essentially complete freedom of movement in flexion, extension, inversion and eversion.

In the preferred embodiment, the convex bearing surface 32 is substantially smaller than the concave bearing surface 20, such that any abrasive materials which may come between the bearing surfaces are free to fall or work their way free of the bearing surface area.

The preferred technique for insertion is as follows: after the usual skin preparation, draping and Esmarch exsanguination of the extremity, an eight inch incision is made longitudinally down the front of the ankle one finger breadth lateral to the crest of the tibia. Dissection is carried down through the soft tissue. The extensor retinaculum is divided longitudinally. The extensor hallucis longus tendon is pulled laterally and the interval between the anterior tibial and extensor hallucis longus is developed. The anterior tibial vessel and nerve are retracted laterally.

The anterior periosteum and capsule of the distal tibia and ankle joint are opened longitudinally and reflected medially and laterally from the tibia and talus. The ankle is then flexed and inspected. A defect or recess is created in the distal tibia measuring one inch in width and three-eighths of an inch in height (dimensions for one embodiment). This defect is centered over the articular surface of the talus. If bone loss is present, either from fracture or severe rheumatoid disease, decrease in the depth will have to be made according to the amount of bone loss present.

A groove is created in the articular surface of the talus from front to back, measuring three-sixteenths of an inch in width and one-half inch in depth, to receive the stem or bonding portion of the talar unit of the prosthesis.

Care is taken to preserve the posterior cortex of the tibia inasmuch as this will prevent extrusion of the cement into the soft tissue behind the tibia. A ⅜ inch drill is used to create the holes in the tibia for better attachment of the cement. A trial fit is mandatory. The tibial unit should fit only when the joint is distracted by manual traction on the foot. This separates all of the joint surfaces. The talar portion is inserted first and cemented into place. The cement is allowed to harden. Next, the tibial unit is inserted into the defect. It is an advantageous feature of this invention that insertion of the tibial unit can be made easily into place centrally over the talar unit since the spherical convex surface of the talar unit can enter the convex axial opening of the partially cylindrical surface of the tibial unit along the sagittal plane without requiring significant manipulation. The tibial portion is then cemented in place. Only a small amount of cement is used in the posterior part of the defect to prevent excessive cement from falling into the posterior portion of the joint. Excess cement must be removed from the convex bearing surface of the talar unit prior to insertion of the tibial unit. The foot is alternately flexed and extended while the cement hardens to prevent glue buildup in the posterior joint.

Routine wound closure is accomplished and a Robert Jones dressing applied with plaster splints. Motion is started on the third post-operative day.

While the preferred form of the invention has been illustrated and described, it should be understood that variations will be apparent to one skilled in the art without departing from the principles described herein. Accordingly, the invention is not to be limited to the specific embodiment illustrated.

The embodiments of the invention in which a particular property or privilege is claimed are defined as follows:

1. An ankle arthroplasty for a human being having a diseased, damaged, or otherwise malfunctioning tibia or talus, comprising:

a tibial unit having an upper bonding surface adapted to be imbedded within the tibia and secured thereto, a lower talar unit having a lower surface adapted to be imbedded with the talus and secured thereto, and opposed, arcuate surface means on said tibial and talar units for providing at least arcuate sliding between the two units in a transverse vertical plane and arcuate fore and aft sliding movement in the sagittal plane, one of said opposed arcuate surfaces being a portion of a cyinder and the other being a portion of a sphere having a radius less than the radius of the cylinder portion, whereby one arcuate surface can rock on the other arcuate surface.

2. The ankle arthroplasty of claim 1, said lower talar unit including said convex spherical portion, said upper tibial portion having said concave, partially cylindrical portion.

3. The ankle arthroplasty of claim 1, said upper tibial unit having a large, concave, partially cylindrical surface, said lower talar unit having a convex, partially spherical surface of substantially smaller arcuate surface area than said partially cylindrical surface for clearing loose foreign matter away from said convex and concave surfaces.

4. A total ankle prosthesis for implantation between the tibia and talus, comprising:

a tibial unit having an upper roughened portion for bonding to the tibia and a lower concave surface forming a portion of a cylinder and having its longitudinal axis lying generally in the sagittal plane, a talar unit having a lower roughened portion for bonding to the talus and an upper convex surface forming a portion of a sphere of a radius less than the radius of the arcuate portion of the tibial unit, and means for securing the tibial and talar units to the tibia and talus, respectively, with the concave surface of the tibial unit abutting and being generally centered against the convex surface of the talar unit, whereby the foot can be moved in flexion, extension, inversion and eversion through combined rocking, sliding and rotational relative movement of the tibial and talar units.

* * * * *